United States Patent
Pfeiffer et al.

(10) Patent No.: US 8,343,058 B2
(45) Date of Patent: Jan. 1, 2013

(54) DILUTION APPARATUS, METHOD AND COMPUTER PROGRAM

(75) Inventors: Ulrich Pfeiffer, Munich (DE); Reinhold Knoll, Munich (DE)

(73) Assignee: Edwards Lifesciences IPRM AG, Nyon (CH)

( * ) Notice: Subject to any disclaimer, the term of this patent is extended or adjusted under 35 U.S.C. 154(b) by 1693 days.

(21) Appl. No.: 11/637,373

(22) Filed: Dec. 12, 2006

(65) Prior Publication Data

US 2007/0135716 A1    Jun. 14, 2007

(30) Foreign Application Priority Data

Dec. 13, 2005    (DE) .................... 10 2005 059 520

(51) Int. Cl.
*A61B 5/08*    (2006.01)
*A61B 5/02*    (2006.01)

(52) U.S. Cl. .................. 600/484; 600/481; 600/483

(58) Field of Classification Search ............. 600/481, 600/484, 504–507, 526
See application file for complete search history.

(56) References Cited

U.S. PATENT DOCUMENTS

| | | | |
|---|---|---|---|
| 5,526,817 A * | 6/1996 | Pfeiffer et al. | 600/504 |
| 5,595,181 A | 1/1997 | Hubbard | 128/692 |
| 6,537,230 B1 | 3/2003 | Pfeiffer et al. | 600/526 |
| 2005/0267378 A1 | 12/2005 | Pfeiffer et al. | 600/526 |

FOREIGN PATENT DOCUMENTS

| | | |
|---|---|---|
| DE | 600 10 224 T2 | 4/2004 |
| EP | 1 139 867 B1 | 10/2001 |
| EP | 1 797 820 B1 | 5/2009 |
| WO | 0130237 | 3/2001 |

OTHER PUBLICATIONS

Monnet et al. "Assessing pulmonary permeability by transpulmonary thermodilution allows differentiation of hydrostatic pulmonary edema from ALI/ARDS". Intensive Care Med (2007) 33:448-453.*
Japanese Office Action, Aug. 26, 2011.
146 pages extracted from European Patent Register for European Patent No. 1 797 820 B1.
Newman EJ et al, "The dye dilution Method for Describing the Central Circulation", Circulation. Nov. 1951;4(5):735-46, available at http://circ.ahajournals.org/cgi/reprint/4/5/735.pdf.

* cited by examiner

*Primary Examiner* — Michael Kahelin
*Assistant Examiner* — Christian Jang
(74) *Attorney, Agent, or Firm* — Michael Crapenhoft

(57) ABSTRACT

An apparatus for determining a patient's circulatory fill status is adapted to provide a dilution curve and is capable to derive the ratio between the patient's global end-diastolic volume GEDV and the patient's intra thoracic thermo volume ITTV from the dilution curve. Further, a computer program for determining a patient's circulatory fill status has instructions adapted to carry out the steps of generating the dilution curve on basis of provided measurement data of dilution versus time, deriving the ratio between the patient's global end-diastolic volume GEDV and the patient's intra thoracic thermo volume ITTV from the dilution curve, and determining the patient's circulatory fill status on basis of the ratio between the patient's global end-diastolic volume GEDV and the patient's intra thoracic thermo volume ITTV, when the computer program is run on a computer. A method is also provided.

7 Claims, 3 Drawing Sheets

DILUTION APPARATUS, METHOD AND COMPUTER PROGRAM

Priority is claimed to German patent application DE 10 2005 059 520.0, filed Dec. 13, 2005, the entire disclosure of which is hereby incorporated by reference herein.

The present invention relates to an apparatus and a computer program for determining a patient's circulatory fill status represented by global end-diastolic volume GEDV, by making use of dilution.

BACKGROUND

It is generally known that in the critical-care diagnosis and treatment of extremely sick persons, cardiac output CO (i.e. blood flow) and circulatory fill volume of a patient's circulatory system are important characteristics for monitoring the patient's state of health.

According to the current state of the art the cardiac output CO can be determined by using a dilution measurement. A bolus of an indicator defined by a predetermined quantity m of the indicator is injected into the patient's vena cava superior, and the indicator concentration c response is measured at a downstream location of the patient's systemic circulation, e.g. at patient's femoral artery. Based on the indicator concentration c response measurement versus time t the dilution curve is generated by plotting the indicator concentration c response as a function of time t.

A schematic example of the dilution curve is illustrated in FIG. 2, wherein the abscissa (time axis) and the ordinate (indicator concentration axis) are of linear scale.

Using the dilution curve, the cardiac output CO is defined as $$CO = \frac{m}{\int c \, dt},$$

wherein m is the indicator amount, c is the indicator concentration, and CO is the cardiac output.

As known from prior art, the sum of circulating volumes $\Sigma V_i$ between the location of injection of the indicator quantity m and the location of measurement of the indicator concentration c response is a specific parameter for estimating circulatory filling. Referring to FIG. 1, the sum of circulation volumes $\Sigma V_i$ encompasses the right-atrial end-diastolic volume $V_2$, the right-ventricular end-diastolic volume $V_4$, the blood volume of the lungs $V_1$, left-atrial end-diastolic volume $V_3$, the left-ventricular end-diastolic volume $V_5$. The largest volume of the group of the circulation volumes $V_{1,\ldots,5}$ is the blood volume of the lungs $V_1$.

The sum of circulating volumes $\Sigma V_i$ can be derived from the dilution curve by calculating $$\sum V_i = CO \cdot MTT,$$

$$MTT = \frac{\int c \cdot t \, dt}{\int c \, dt},$$

wherein $\Sigma V_i$ is the sum of circulating volumes and MTT is the mean transit time defined as being the centre of mass of the dilution curve area.

It is generally known that the circulation volumes $V_{2,\ldots,5}$ related to the heart indicate the circulatory fill status of a person. The sum of relevant circulation volumes $\Sigma V_{2,\ldots,5}$ can be derived from $$\Sigma V_{2,\ldots,5} = \Sigma V_i - V_1.$$

It is known from Newman et al (Circulation 1951 November; 4(5):735) that the largest volume $V_1$ can be calculated by approaching a mono exponential function to the down slope part of the concentration curve. The time constant of this function is called down slope time DST. I.e., the down slope time DST is the time the indicator concentration takes to drop by the factor of $e^{-1}$.

Therefore, the largest volume $V_1$ can be calculated by $$V_1 = CO \cdot DST,$$

$$c = const \cdot e^{\frac{-t}{DST}},$$

wherein CO is the cardiac output and DST is the down slope time.

It is common to use cooling energy as indicator for generating the dilution curve by injecting a cold liquid central venous and measuring the resulting temperature change in the aorta. In this case, dilution is called transpulmonary thermo-dilution.

In the case of transpulmonary thermo-dilution, $\Sigma V_i$ is called intra thoracic thermo volume ITTV, and the largest volume in the circulation $V_1$ is called pulmonary thermo volume PTV.

In this respect, above mentioned equations can be read as $$ITTV = CO \cdot MTT,$$

and $$PTV = CO \cdot DST.$$

From U.S. Pat. No. 5,526,817 it is known that the global end-diastolic volume GEDV reflects the sum of the ventricle volumes, i.e. the sum of the smaller mixing volumes, without the lung volume, i.e. the largest mixing volume. These volumes essentially correspond to the end-diastolic cardiac volumes. The global end-diastolic volume GEDV can be determined from the thermo-dilution curve, i.e. from e.g. the difference between the intra thoracic thermo volume ITTV and the pulmonary thermo volume PTV, which could be derived from the difference between the mean transit time MTT and the down slope time DST, multiplied by the cardiac output CO, i.e.

$$GEDV = ITTV - PTV = CO \cdot (MTT - DST).$$

As mentioned above, when calculating the values of the cardiac output CO and the mean transit time MTT by making use of the thermo-dilution curve, the indicator concentration c is integrated over the time t. In order to get accurate results, the measurements of the indicator concentration over the time t are required not to be affected by interfering effects.

However, the decay part of thermo-dilution curve is superposed by blood recirculation flow. Therefore, on the one hand, it is useful to abort the measurement of the indicator concentration c before this recirculation flow occurs at the measurement location.

Further, the thermo-dilution curve converges to the mono exponential function as above mentioned just after a quite long period of time. Therefore, on the other hand, it is useful to calculate the down slope time DST at high time-coordinates.

Therefore, in order to overcome these disadvantages, usually, when performing the measurement of the indicator concentration c, the thermo-dilution curve is recorded until a level of 40% of the maximum dilution value is reached. Further, the down slope time DST is then estimated from the section of the dilution curve usually comprising 60% to 40% of the maximum dilution value by extrapolating the remaining decay curve (indicated in FIG. 2 as dotted line).

However, this extrapolation is erroneous. When having unfavorable circumstances, this down slope time DST value estimated by extrapolation of the dilution curve could differ up to 30% from the corresponding proper value at high time-coordinates.

Further, since the mean transit time MTT is defined as including a multiplication with the time t, errors in extrapolating the dilution curve are affecting the accuracy of the value of the mean transit time MTT.

Consequently, inaccurate values of the down slope time DST and the mean transit time MTT reduce the accurateness of the global end-diastolic volume GEDV calculated from these values.

Furthermore, referring to FIG. 2, the dilution curve is superposed by a baseline temperature drift. The dilution curve is asymptotically approaching the level of the baseline temperature extrapolation. In order to extrapolate the decay of the dilution curve properly, the baseline temperature drift has to be taken into account. The baseline temperature drift has to be estimated before the injection of the indicator.

The extrapolation of the baseline temperature drift is indicated in FIG. 2 as dotted line. With increasing time-coordinate the extrapolation of the baseline temperature drift becomes inaccurate thereby affecting the accuracy of the calculated values of the down slope time DST and the mean transit time MTT.

SUMMARY OF THE INVENTION

It is an object of the present invention to provide an apparatus and a computer program for determining a patient's circulatory fill status by making use of dilution, in particular transpulmonary dilution, wherein the patient's circulatory fill status can be determined accurately.

The present invention provides an apparatus for determining a patient's circulatory fill status, wherein the apparatus is adapted to provide a dilution curve and is capable of deriving the ratio between the patient's global end-diastolic volume GEDV and the patient's intra thoracic thermo volume ITTV from the dilution curve.

The present invention also provides a method for determining a patient's circulatory fill status, comprising the steps of determining a dilution curve and deriving the ratio between the patient's global end-diastolic volume GEDV and the patient's intra thoracic thermo volume ITTV from the dilution curve.

Further, the present invention provides a computer program for determining a patient's circulatory fill status. The computer program has instructions adapted to carry out the steps of generating the dilution curve on basis of provided measurement data of dilution versus time, deriving the ratio between the patient's global end-diastolic volume GEDV and the patient's intra thoracic thermo volume ITTV from the dilution curve, and determining the patient's circulatory fill status on basis of the ratio between the patient's global end-diastolic volume GEDV and the patient's intra thoracic thermo volume ITTV, when the computer program is run on a computer.

Due to the fact that according to the present invention determining the patient's circulatory fill status by making use of dilution is based on the ratio between the patient's global end-diastolic volume GEDV and the patient's intra thoracic thermo volume ITTV, the patient's circulatory fill status can be determined accurately. Therefore, reliable monitoring the patient's state of health in the critical-care diagnosis and treatment of extremely sick persons is possible.

Preferably the apparatus and method are adapted to determine the ratio between the patient's global end-diastolic volume GEDV and the patient's intra thoracic thermo volume ITTV using the ratio between the median transit time MDT and the mean transit time MTT, wherein the median transit time MDT is defined as being the point of time on which half of the dilution curve area is reached and the mean transit time MTT is defined as being the point of time on which the center of mass of the dilution curve area is located, and wherein the apparatus is capable of deriving the ratio between the median transit time MDT and the mean transit time MTT from the dilution curve.

Further, according to a preferred embodiment of the present invention, the computer program carries out the steps of determining the median transit time MDT and the mean transit time MTT, determining the ratio between the median transit time MDT and the mean transit time MTT, determining the ratio between the patient's global end-diastolic volume GEDV and the patient's intra thoracic thermo volume ITTV using the ratio between the median transit time MDT and the mean transit time MTT.

Determining the ratio between the patient's global end-diastolic volume GEDV and the patient's intra thoracic thermo volume ITTV using the ratio between the median transit time MDT and the mean transit time MTT may be advantageous, since thereby the ratio between the patient's global end-diastolic volume GEDV and the patient's intra thoracic thermo volume ITTV is less effected by temperature drift and blood recirculation. Therefore, the ratio between the patient's global end-diastolic volume GEDV and the patient's intra thoracic thermo volume ITTV can be calculated accurate and hence used as reliable parameter for monitoring patient's health state.

Preferably, for determining the ratio between the patient's global end-diastolic volume GEDV and the patient's intra thoracic thermo volume ITTV, the apparatus, method and computer program make use of a nearly linear relationship between the ratio between the patient's global end-diastolic volume GEDV and the patient's intra thoracic thermo volume ITTV, and the ratio between the median transit time MDT and the mean transit time MTT.

Further, preferably the apparatus, method and computer program make use of the equation $$\frac{MDT}{MTT} = a + b \cdot \frac{GEDV}{ITTV},$$

wherein parameters a and b are set to be $a \approx \ln 2$ and $b \approx 1 - \ln 2$.

Furthermore, it is preferred that alternatively the parameters a and b are set to be $a \approx 0.686$ and $b \approx 0.377$.

As an alternative embodiment, preferably the apparatus, method and computer program determine the ratio between the patient's global end-diastolic volume GEDV and the patient's intra thoracic thermo volume ITTV using the degree of asymmetry of the shape of the dilution curve.

Determining the ratio between the patient's global end-diastolic volume GEDV and the patient's intra thoracic thermo volume ITTV using of the degree of asymmetry of the shape of the dilution curve may be advantageous, since thereby the ratio between the patient's global end-diastolic volume GEDV and the patient's intra thoracic thermo volume ITTV is less effected by temperature drift and blood recirculation. Therefore, the ratio between the patient's global end-diastolic volume GEDV and the patient's intra thoracic thermo volume ITTV can be calculated accurate and hence used as reliable parameter for monitoring patient's health state.

Additionally, it is preferred that the apparatus and the computer program determine the degree of asymmetry of the shape of the dilution curve by means of the ratio SR between the slopes of the dilution curve occurring in both inflection points $t_u$, $t_d$ thereof.

Preferably, the apparatus, method and computer program determine the degree of asymmetry of the shape of the dilution curve by making use of the equations $$\alpha := \frac{GEDV}{ITTV};$$

$$SR := \frac{dc/dt(t_d)}{dc/dt(t_u)} = \frac{-\alpha}{1-2\alpha} e^{\frac{\alpha}{1-2\alpha} \ln\left(\frac{1-\alpha}{\alpha}\right)^2} + \frac{1-\alpha}{1-2\alpha} e^{\frac{1-\alpha}{1-2\alpha} \ln\left(\frac{1-\alpha}{\alpha}\right)^2}.$$

Additionally, it is preferred that for determining the distribution of the patient's heart volumes the apparatus, method and the computer program make use of the shape of the dilution curve.

Preferably, the apparatus, method and computer program determine the peak shape PS of the dilution curve for estimating the shape of the dilution curve, wherein the peak shape PS is defined as being the ratio between the minimum curvature radius $k_{min}$ of the dilution curve and the peak height $c_{max}$ of the dilution curve, wherein the curvature radius k of the dilution curve is defined as being $$k = \frac{(1+(dc/dt)^2)^{3/2}}{d^2c/dt^2}.$$

BRIEF DESCRIPTION OF THE DRAWINGS

In the following the invention is explained on the basis of a preferred embodiment with reference to the drawings. In the drawings.

DETAILED DESCRIPTION

Figure 2:
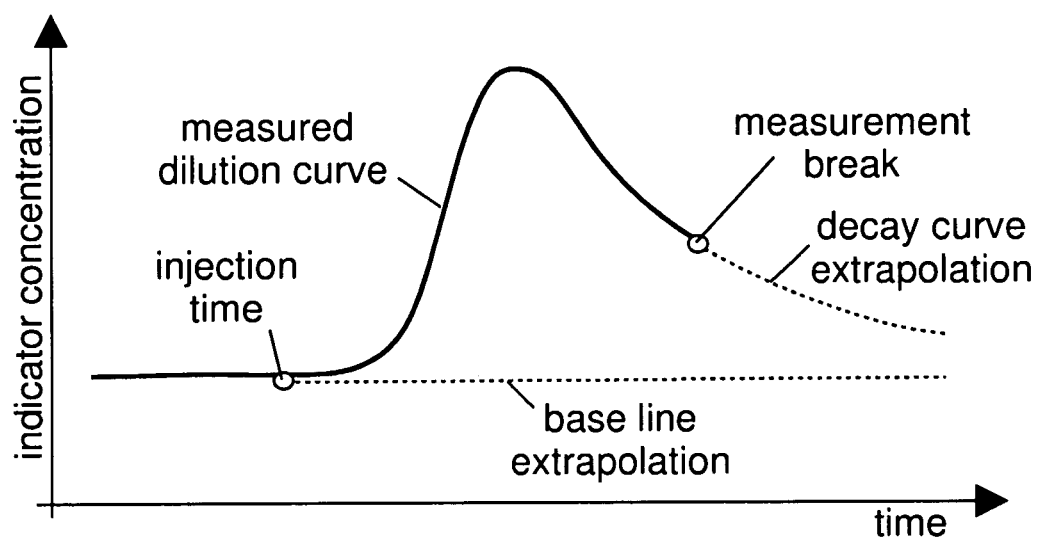
FIG. 2 shows a dilution curve.

FIG. 2 shows the plot of a dilution curve, i.e. a graph of measured data of an indicator concentration versus time, wherein the indicator concentration axis is the ordinate and the time axis is the abscissa. Both axes are of linear scale.

Following the time axis and starting from the abscissa, at first the dilution curve forms the base line being substantially parallel to the time axis.

After having carried out an injection of the indicator into a patient's vena, the dilution curve starts to rise until a maximum value has been reached. After having passed this maximum value the dilution curve drops.

Until then the dilution curve is generated by using measured indicator concentration values.

When the dilution curve has reached the level of 40% of the difference between the maximum point and the base line (measurement break in FIG. 2), the dilution curve is no longer generated by measured indicator data but by an extrapolated decay curve.

The extrapolated decay curve is defined by an exponential function asymptotically approaching an extrapolated line of the base line. The time constant of the exponential function is called down slope time DST and is obtained in making use of a section of the dilution curve between the measurement break and the indicator concentration value at 60% of the maximum value.

The median transit time MDT is defined as being the time when half of the dilution curve area is reached. The mean transit time MTT is defined as being the center of mass of the dilution curve area.

It was found that there is approximately a linear relation between the median transit time MDT and the mean transit time MTT and the remaining minor volumes in the circulation which are associated with the sum of the heart volumes which is called global end-diastolic volume GEDV.

Therefore, the global end-diastolic volume GEDV is calculated by a linear function of the mean transit time MTT and the median transit time MDT. Hence, the volume ratio GEDV relative to ITTV is calculated as $$\frac{MDT}{MTT} = a + b \cdot \left(\frac{GEDV}{ITTV}\right),$$

and $$\frac{GEDV}{ITTV} = \frac{1}{b} \cdot \left(\frac{MDT}{MMT} - a\right),$$

respectively.

The constants a and b are empirically determined and are dependent on the type of circulation.

A device for calculating such equations may be for example similar to that shown in U.S. Pat. No. 5,526,817, hereby incorporated by reference herein, with a processor or computer programmed to run the program described herein.

Figure 1:
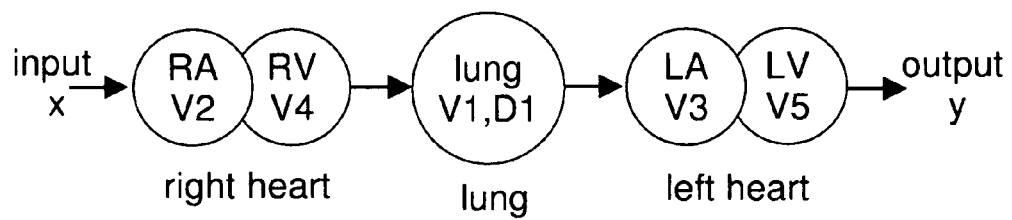
FIG. 1 shows a model of the pulmonary circulation.

FIG. 1 shows a model of a pulmonary circulation with a large volume $V_1$ and a delay $D_1$ which represent the lung, and smaller volumes $V_2$, $V_4$, which represent the atrium and the ventricle of the right heart and smaller volumes $V_3$, $V_5$, which represent the atrium and the ventricle of the left heart. For the sake of simplification, a fixed ratio of $V_2:V_4$ and $V_3:V_5$ is assumed.

As a first approximation, it is assumed that the volume $V_1$ is dominant, the volume $V_2$ is minor and all other volumes are neglectable. Therefore, the constants a and b are to be set as $a \approx \ln 2$ and $b \approx 1 - \ln 2$.

However, this first approximation is a rough estimate only. In order to obtain a more accurate mathematical model of the pulmonary system, the mixing volumes $V_i$ and the delays $D_i$ are combined. The delays could be considered by transforming the time coordinate and are summarized to a single delay.

The lung is modeled by the volume $V_1$ and the delay $D_1$. The right heart is modeled by the volumes $V_2$ and $V_4$ which are representing the right atrium and the right ventricle, respectively. The left heart is modeled by the volumes $V_3$ and $V_5$ which are representing the left atrium and the left ventricle, respectively.

The system output y, i.e. the concentration at the downstream location, could be found by convolution of the system input x, i.e. the indicator injection and the system responses of the individual elements.

For the sake of convenience, the indicator amount for the curve area is chosen to be "1". For other indicator quantities the system output y is multiplied by a constant factor. The preferred model of the pulmonary system of FIG. 1 provides $$V_1 = \frac{1}{\tau_1} \cdot e^{\frac{-t}{\tau_1}},$$

$$V_2 = \frac{1}{\tau_2} \cdot e^{\frac{-t}{\tau_2}},$$

$$V_3 = \frac{1}{\tau_3} \cdot e^{\frac{-t}{\tau_3}},$$

$$V_4 = \frac{1}{\tau_4} \cdot e^{\frac{-t}{\tau_4}},$$

$$V_5 = \frac{1}{\tau_5} \cdot e^{\frac{-t}{\tau_5}},$$

and $$y = x * S_{rightHeart} * S_{Lung} * S_{leftHeart} = x * V2 * V4 * V1 * D1 * V3 * V5.$$

In case of a very short (dirac shaped) injection with $V_1 \gg V_2$ and $V_3 = V_4 = V_5 = 0$ the model results in $$y = \frac{1}{\tau_1 - \tau_2}[e^{-t/\tau_1} - e^{-t/\tau_2}]$$

From this equation MTT and MDT could be calculated analytically $$MTT = \tau_1 + \tau_2$$

$$MDT \approx \tau_1 \ln\left(\frac{2\tau_1}{\tau_1 - \tau_2}\right) \approx \tau_1 \ln(2) + \tau_2$$

$$\frac{MDT}{MTT} \approx \ln(2) + \frac{\tau_2(1 - \ln(2))}{\tau_1 + \tau_2}$$

$$\frac{MDT}{MTT} \approx \ln(2) + (1 - \ln(2))\frac{GEDV}{ITTV}$$

In case of a very short (dirac shaped) injection and $V_2 = V_4$ not equal to $V_3 = V_5$ the model results in $$y = \frac{\tau_1^3}{(\tau_1 - \tau_3)^2(\tau_1 - \tau_2)^2}\exp^{-t/\tau_1} - \frac{\tau_2\left(t + \frac{\tau_1\tau_2}{\tau_1 - \tau_2} + 2\frac{\tau_3\tau_2}{\tau_3 - \tau_2}\right)}{(\tau_1 - \tau_2)(\tau_3 - \tau_2)^2}\exp^{-t/\tau_2} - \frac{\tau_3\left(t + \frac{\tau_1\tau_3}{\tau_1 - \tau_3} - 2\frac{\tau_3\tau_2}{\tau_3 - \tau_2}\right)}{(\tau_1 - \tau_3)(\tau_3 - \tau_2)^2}\exp^{-t/\tau_3}$$

From this equation MDT and MTT could be calculated with sets of volumes which could be found in real life. A linear regression of these various situations provides $$\frac{MDT}{MTT} = a + b \cdot \frac{GEDV}{ITTV}$$

$$a \approx 0.686$$

$$b \approx 0.377$$

In order to substitute the mean transit time MTT these relations could be also used in combination with the prior art equation $$GEDV = CO \cdot (MTT - DST).$$

The GEDV versus ITTV ratio can be alternatively calculated from the degree of asymmetry of the shape of the dilution curve.

The degree of asymmetry is defined by means of the slope ratio SR of maximum up slope versus maximum down slope of the dilution curve.

Figure 3:
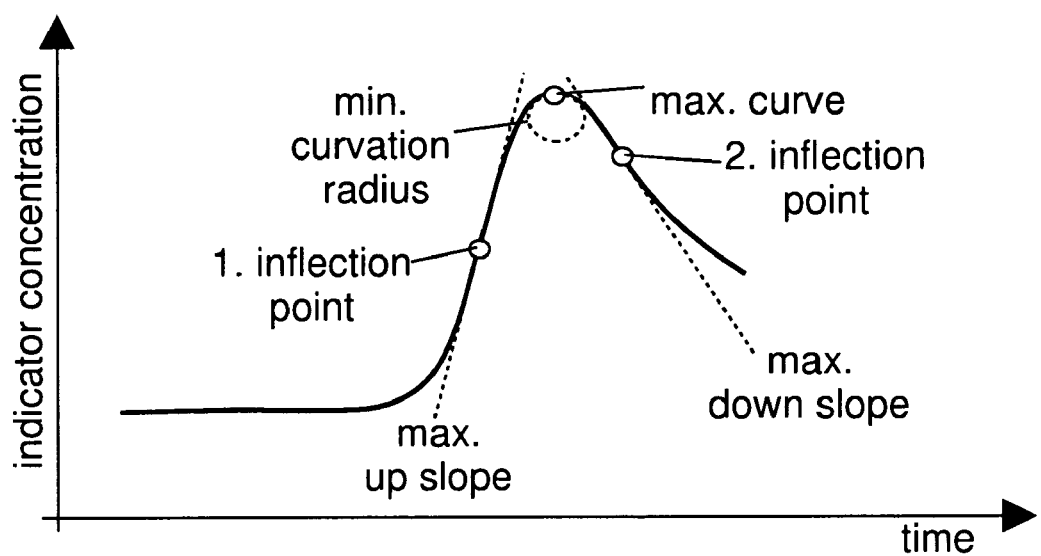
FIG. 3 shows the dilution curve of FIG. 2 with maximum up slope, maximum down slope and peak shape.

FIG. 3 shows the dilution curve with maximum up slope occurring at the first inflection point $t_u$ and the maximum down slope occurring at the second inflection point $t_d$.

As a first approximation, it is assumed that volume $V_1$ is dominant, volume $V_2$ is minor and all other volumes are neglectable. Therefore, the global end-diastolic volume GEDV is determined by the reverse function of the slope ratio SR, i.e.

$$\alpha := \frac{GEDV}{ITTV};$$

$$SR := \frac{dc/dt(t_d)}{dc/dt(t_u)} = \frac{-\alpha}{1 - 2\alpha}e^{\frac{\alpha}{1-2\alpha}\ln\left(\frac{1-\alpha}{\alpha}\right)^2} + \frac{1-\alpha}{1-2\alpha}e^{\frac{1-\alpha}{1-2\alpha}\ln\left(\frac{1-\alpha}{\alpha}\right)^2}.$$

The reverse function can be implemented by a lookup table or splines.

More accurate functions can be found using of empirically corrections for real circulations.

Furthermore, the shape of the dilution peak of the dilution curve can be used to determine the distribution of the heart volumes. Normally the heart volumes have approximately the same size, but pathological enlargements of one or more heart chambers can occur. In this case, the dilution peak of the dilution curve is more round than normal. If this degree of peak roundness is above a certain limit a message could be given to a doctor in order to perform further diagnosis. The peak shape PS is defined using the minimum curvature radius $k_{min}$ over the peak height $c_{max}$, i.e.

$$k = \frac{(1 + (dc/dt)^2)^{3/2}}{d^2c/dt^2}$$

and $$PS = \frac{k_{min}}{c_{max}}.$$

Taking above mentioned and described modelling into account, a process for determining the patient's circulatory fill status comprises the steps:

Generating a dilution curve on basis of provided measurement data of dilution versus time.

Determining the median transit time MDT being defined as the point of time on which half of the dilution curve area is reached, and the mean transit time MTT being defined as the point of time on which the centre of mass of the dilution curve area is located.

Determining the ratio between the patient's global end-diastolic volume GEDV and the patient's intra thoracic thermo volume ITTV using the ratio between the median transit time MDT and the mean transit time MTT by making use of the equation $$\frac{MDT}{MTT} = a + b \cdot \frac{GEDV}{ITTV},$$

wherein parameters a and b are set to be $a \approx \ln 2$  $b \approx 1 - \ln 2$ or alternatively $a \approx 0.686$  $b \approx 0.377$.

Determining the patient's circulatory fill status on basis of the ratio between the patient's global end-diastolic volume GEDV and the patient's intra thoracic thermo volume ITTV.

Further, taking above mentioned and described modelling into account, an alternative process for determining the patient's circulatory fill status comprises the steps:

Generating a dilution curve on basis of provided measurement data of dilution versus time.

Determining the degree of asymmetry of the shape of the dilution curve by means of the ratio SR between the slopes of the dilution curve occurring in both inflection points tu, td thereof by making use of the equations $$\alpha := \frac{GEDV}{ITTV};$$

$$SR := \frac{dc/dt(t_d)}{dc/dt(t_u)} = \frac{-\alpha}{1-2\alpha}e^{\frac{\alpha}{1-2\alpha}\ln\left(\frac{1-\alpha}{\alpha}\right)^2} + \frac{1-\alpha}{1-2\alpha}e^{\frac{1-\alpha}{1-2\alpha}\ln\left(\frac{1-\alpha}{\alpha}\right)^2}.$$

Determining the patient's circulatory fill status on basis of the degree of asymmetry of the shape of the dilution curve.

Furthermore, taking above mentioned and described modelling into account, a process for determining the distribution of the patient's heart volumes comprises the steps:

Generating a dilution curve on basis of provided measurement data of dilution versus time.

Determining peak shape PS of the dilution curve being defined as the ratio between the minimum curvation radius kmin of the dilution curve and the peak height cmax of the dilution curve, wherein the curvation radius k of the dilution curve is defined as being $$k = \frac{(1+(dc/dt)^2)^{3/2}}{d^2c/dt^2}.$$

Using the peak shape PS of the dilution curve for determining the distribution of the patient's heart volumes.

What is claimed is:

1. An apparatus for determining a patient's circulatory fill status comprising:
 a device configured to provide a dilution curve and configured to derive a ratio between a patient's global end-diastolic volume (GEDV) and a patient's intra thoracic thermo volume (ITTV) using a degree of asymmetry of the shape of the dilution curve,
 said device further configured to determine the patient's circulatory fill status based at least in part on the ratio between the patient's global end-diastolic volume (GEDV) and the patient's intra thoracic thermo volume (ITTV).

2. The apparatus according to claim 1, wherein the apparatus is configured to determine the degree of asymmetry of the shape of the dilution curve by determining the ratio (SR) between the slopes of the dilution curve occurring in both inflection points ($t_u$, $t_d$) thereof.

3. The apparatus according to claim 2, wherein the apparatus is configured to determine the degree of asymmetry of the shape of the dilution curve by calculating the equations $$\alpha := \frac{GEDV}{ITTV};$$

$$SR := \frac{dc/dt(t_d)}{dc/dt(t_u)} = \frac{-\alpha}{1-2\alpha}e^{\frac{\alpha}{1-2\alpha}\ln\left(\frac{1-\alpha}{\alpha}\right)^2} + \frac{1-\alpha}{1-2\alpha}e^{\frac{1-\alpha}{1-2\alpha}\ln\left(\frac{1-\alpha}{\alpha}\right)^2}.$$

4. A non-transitory computer readable medium having embodied thereon a program for determining a patient's fill status, which when executed by a computer, causes the computer to execute a method comprising:
 generating a dilution curve based at least in part on provided measurement data of dilution versus time,
 determining a degree of asymmetry of the shape of the dilution curve,
 determining a ratio between the patient's global end-diastolic volume (GEDV) and the patient's intra thoracic thereto volume (ITTV) using the degree of asymmetry of the shape of the dilution curve, and
 determining the patient's circulatory fill status based at least in part on the ratio between the patient's global end-diastolic volume (GEDV) and the patient's intra thoracic thermo volume (ITTV).

5. The non-transitory computer readable medium of claim 4, wherein the degree of asymmetry of the shape of the dilution curve is determined based at least in part on the ratio (SR) between the slopes of the dilution curve occurring in both inflection points ($t_u$, $t_d$) thereof.

6. The non-transitory computer readable medium of claim 5, wherein the degree of asymmetry of the shape of the dilution curve is determined based at least in part on calculating the equations:

$$\alpha := \frac{GEDV}{ITTV};$$

$$SR := \frac{dc/dt(t_d)}{dc/dt(t_u)} = \frac{-\alpha}{1-2\alpha}e^{\frac{\alpha}{1-2\alpha}\ln\left(\frac{1-\alpha}{\alpha}\right)^2} + \frac{1-\alpha}{1-2\alpha}e^{\frac{1-\alpha}{1-2\alpha}\ln\left(\frac{1-\alpha}{\alpha}\right)^2}.$$

7. A computer-implemented method for determining a patient's circulatory fill status, the method comprising:
 running a program on a computer, said program including instructions adapted to carry out the steps of:
  generating a dilution curve based at least in part on provided measurement data of dilution versus time,
  determining a degree of asymmetry of the shape of the dilution curve,
  determining a ratio between the patient's global end-diastolic volume (GEDV) and the patient's intra thoracic thermo volume (ITTV) using the degree of asymmetry of the shape of the dilution curve, and
  determining the patient's circulatory fill status based at least in part on the ratio between the patient's global end-diastolic volume (GEDV) and the patient's intra thoracic thermo volume (ITTV).

* * * * *